United States Patent
Ishihara et al.

[11] Patent Number: 5,934,278
[45] Date of Patent: Aug. 10, 1999

[54] NON-INVASIVE BLOOD ANALYZER

[75] Inventors: Ken Ishihara, Takarazuka; Kaoru Asano, Kobe; Yasunori Maekawa, Miki, all of Japan

[73] Assignee: TOA Medical Electronics Co., Ltd., Hyogo, Japan

[21] Appl. No.: 08/442,654

[22] Filed: May 16, 1995

[30]  Foreign Application Priority Data

May 17, 1994 [JP] Japan ................................ 6-128180

[51] Int. Cl.$^6$ ........................................................ A61B 6/00
[52] U.S. Cl. ........................ 128/665; 128/633; 128/637; 356/39
[58] Field of Search .................................. 128/664, 665, 128/633, 637; 356/39, 40, 433, 239

[56]  References Cited

U.S. PATENT DOCUMENTS

| | | | |
|---|---|---|---|
| 4,453,266 | 6/1984 | Bacus | 356/39 |
| 4,998,533 | 3/1991 | Winkelman . | |
| 5,137,355 | 8/1992 | Barbour et al. | 356/342 |
| 5,394,199 | 2/1995 | Flower | 128/633 |
| 5,435,307 | 7/1995 | Friauf et al. | 128/633 |
| 5,465,718 | 11/1995 | Hochman et al. | 128/664 |
| 5,490,505 | 2/1996 | Diab et al. | 128/633 |
| 5,490,506 | 2/1996 | Takatani et al. | 128/633 |

FOREIGN PATENT DOCUMENTS 4-161915  6/1992  Japan .

Primary Examiner—Brian L. Casler

[57]   ABSTRACT

A non-invasive blood analyzer includes a light applying device for applying light to a detection region including a blood vessel in a living body and a capturing device for capturing an image of the detection region to which the light is applied. Finally, an analyzing device is included for further processing the captured image to analyze blood cells in the blood vessel included in the detection region. Preferably, the analyzing device includes a reference image forming device for forming a reference image by using at least one of a plurality of images which the capturing device repeatedly captures with respect to the same detection region. In addition, it includes a differential image forming device for calculating a difference in pixel information between the reference image and one of the plurality of images to form a differential image by using the calculated difference as pixel information. Finally, a blood cell image detecting device is included for detecting a blood cell image from the differential image.

11 Claims, 11 Drawing Sheets

FIG. 1

NON-INVASIVE BLOOD ANALYZER

BACKGROUND OF THE INVENTION

1. Field of the Invention

The present invention relates to an apparatus for analyzing blood in a non-invasive manner. More particularly, it relates to an apparatus for optically measuring blood flowing through a living body in order to analyze blood components required for a hematology test.

2. Description of the Prior Art

Hematology tests such as blood cell counting (white blood cell: WBC, red blood cell: RBC, etc), hematocrit (HCT), hemoglobin (HGB), and mean corpuscular constant (mean corpuscular volume: MCV, mean corpuscular hemoglobin: MCH, and mean corpuscular hemoglobin concentration: MCHC) are extremely important for the diagnosis of diseases and the treatment thereof. Such items are most frequently used during the clinical testing of patients.

Such hematology tests involve collecting blood from a patient to analyze the sample thereof with an analyzer. However, the collection of blood from a patient can cause considerable pain to some people. Since a hematology test on the collected blood is not a real-time test, the test result may not provide an accurate diagnosis. In addition, the above hematology test is always accompanied by a fear that needles used for blood collection may be used mistakenly after they have been used for collecting blood from someone who has contracted an infectious disease such as hepatitis or HIV. Thus, there has been a demand for many years for an apparatus that allows practitioners to perform a blood test in a non-invasive manner. When such a blood analyzer is installed beside the patient's bed, practitioners can monitor the patient's conditions on the spot without difficulty. As a prior art relating to such apparatus, a video microscope (for example, as disclosed in Japanese Published Unexamined Patent Application No. HEI 4(1992)-161915) is known which applies light to a portion of a patient's skin in order to photograph a video image thereof (static image) at a shutter speed of about one-thousandth of a second and identifies a discontinuous point in the blood stream where a point moves one by one in a static image. U.S. Pat. No. 4,998,533 (Winkelman) describes an apparatus and method for in vivo determination of red and white blood cell characteristics from a flow of red and white cells in mucous membranes, in which an image capturing device is employed to optically isolate images from a flow of blood cells and transmit those images to an image receiving device for encoding into electronic signals.

In addition, when the blood flowing through blood vessels of a patient are photographed with a conventional video microscope and a dynamic image thereof is observed, cubic and transparent objects such as white blood cells (leukocytes) can be recognized. This may be because the peripheries of the white blood cells have been made conspicuous against the static background.

However, observation of the static image of white blood cells cannot provide a clear particle image because of the virtual absence of optical differences between the white blood cells and the background.

Consequently, a drawback of the conventional video microscope is that it is difficult to make a quantitative analysis of blood cells, and in particular the number of white blood cells.

SUMMARY OF THE INVENTION

The present invention has been made in view of the above, and the object of the invention is to provide an apparatus that allows the analysis of the number of blood cells, particularly white blood cells, from images by photographing such blood cells traveling through blood vessels.

The present invention provides a non-invasive blood analyzer comprising: light applying means for applying light to a detection region including a blood vessel in a living body; capturing means for capturing an image of the detection region to which the light is applied; and analyzing means for processing the captured image to analyze the number of blood cells in the blood vessel included in the detection region. The analyzing means preferably includes, reference image forming means for forming a reference image by using at least one of a plurality of images which the capturing means repeatedly captures with respect to the same detection region; differential image forming means for calculating a difference in pixel information between the reference image and one of the plurality of images to form a differential image by using the calculated difference as pixel information; and blood cell image detecting means for detecting a blood cell image from the differential image.

The blood analyzer is characterized by non-invasively analyzing blood in a living body, and preferably the body of mammals, including human bodies.

Furthermore, from a different viewpoint, the present invention provides a method for non-invasively analyzing blood comprising the steps of; applying light to a detection region including a blood vessel in a living body; capturing an image of the detection region to which the light is applied; forming a reference image by using at least one of a plurality of images which the capturing means repeatedly captures with respect to the same detection region; calculating a difference in pixel information between the reference image and one of the plurality of images to form a differential image by using the calculated difference as pixel information; and detecting a blood cell image from the differential image to analyze the blood cell.

These and other objects of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 is a view illustrating the structure of one embodiment of the present invention;

DESCRIPTION OF THE PREFERRED EMBODIMENTS

Figure 2:
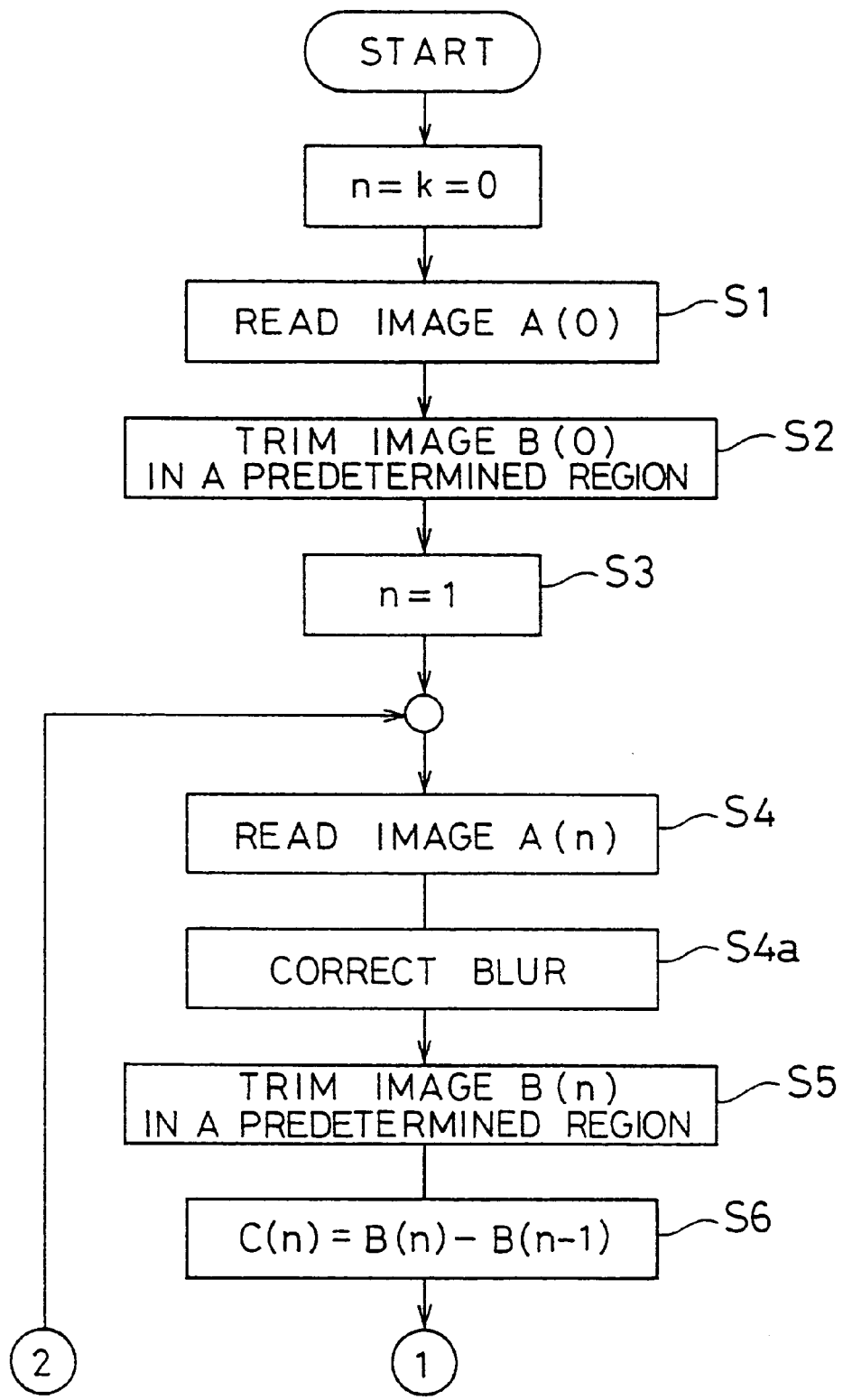
FIGS. 2 and 3 are flowcharts showing a procedure of an embodiment of the present invention.

A detection region, including the blood vessels of a living body, constitutes a target to which light is applied by a light applying device and refers to a predetermined region including blood vessels that are present in the living body. The region does not refer to a part of a living body which has been surgically extracted.

On the other hand, the size of the blood vessels included in the target region are not limited to particular size, but capillaries or arterioles and veinlets located adjacent to the skin are preferable. Incidentally blood cell information obtained in small blood vessels can be translated into information on thick blood vessels (such as large and medium-size blood vessels).

As the light applying device of the present invention, light sources that can continuously apply light such as a laser, a halogen lamp, or a tungsten lamp or an intermittent light source for intermittently applying light, such as a multi-strobe (DSX series model manufactured by Sugawara Laboratories) or a pulse laser (such as the 7000 series model manufactured by Spectra-Physics) can be used.

Furthermore, the light applying device preferably provides (1) an optical fiber, (2) a reflector, (3) a lens or (4) a slit in addition to the light source. However, the above device can be combined in such pairs as (1) and (2), (1) and (3) or (2) and (3) in such triplets as (1), (2) and (3) or (2), (3) and (4) or in such quadruplets as (1), (2), (3) and (4). In such case, a prism can be used in place of the reflector. The light applying device may provide a polarizing device for applying polarizing light to the detection region.

As the capturing device of the present invention, a general CCD image sensor can be used, for example. The capturing device may include an optical system for directing light reflected from the detection region to the CCD image sensor, the optical system having at least one of an optical fiber, a reflector, a polarizer, a lens, a prism, a slit and a filter.

Preferably, the capturing device includes an image intensifier for intensifying the reflected light from the detection region when the reflected light is weak.

Further, the capturing device may include, a signal processing system having a video signal processing circuit for supplying scanning signals to the CCD image sensor and processing video signals output from the CCD image sensor, and a video tape or disk recorder for recording the video signals.

Furthermore, a commercially available video microscope may be used as the light applying device and the capturing device.

As the analyzing device, an image processing computer (for example, a Quadra 800 manufactured by Apple Computer) can be used. However, an analog prepreprocessor (for example, HK-7000 manufactured by Minolta) may be used together to adjust the contrast of an image that has been captured.

In the present invention, the capturing device captures a plurality of images of an identical detection region irradiated with the light applying device. The analyzing device forms a reference image by using at least one of the plurality of images that has been captured, calculates a difference in pixel information between the reference image and one of the plurality of images, and forms a differential image based on the calculated difference. Consequently, in the differential image, the background of the image is erased so that only blood cells are shown. In this manner, even white blood cells can be easily detected by a differential image, even though white blood cells are very difficult to be differentiated from the background.

The plurality of images repeatedly captured by the capturing device here refer to two hundred frames of images consecutively photographed by the video camera in a cycle of one thirtieth of a second. In particular, the kind of the capturing device, the capturing cycle and the number of frames are not specifically restricted to any kind or any level.

Furthermore, the reference image forming device of the analyzing device may select one of the plurality of images that have been captured to use as the reference image. The differential image forming means of the analyzing device may form a differential image from a difference between the reference image and other images.

Additionally, the reference image forming device may form a new reference image every time the differential image forming device forms one differential image. Preferably, the reference image forming device calculates an average of at least two of the plurality of images that have been repeatedly captured to form the reference image by using the average as pixel information.

In the reference image thus obtained, each pixel information is averaged so that the effects due to noise that have been generated by non-uniform illumination and scattered light is suppressed.

By the way, the average may be calculated with respect to all the plurality of images that have been captured or with respect to parts of images that have been arbitrarily sampled out.

Furthermore, the analyzing device may provide binary code processing device to give clearer images, with the binary code processing device coding pixel information on the differential image with a predetermined threshold value.

The analyzing device may further provide a blood cell recognizing device to accurately recognize the kind of blood cells in the images thereof by comparing the images with a predetermined reference image, with particular reference to the number and configuration.

The analyzing device counts the number of blood cell images detected by the blood cell image detecting device out of the plurality of differential images formed by the capturing device in the same predetermined region and in a predetermined cycle. Calculating the distance traveled by the blood cell allows calculation of the number of blood cells per unit volume and the travel speed thereof.

Referring now to the embodiments shown in the accompanying drawings, the present invention will be detailed herein below, but they are not intended to limit the scope of the present invention.

Figure 1:
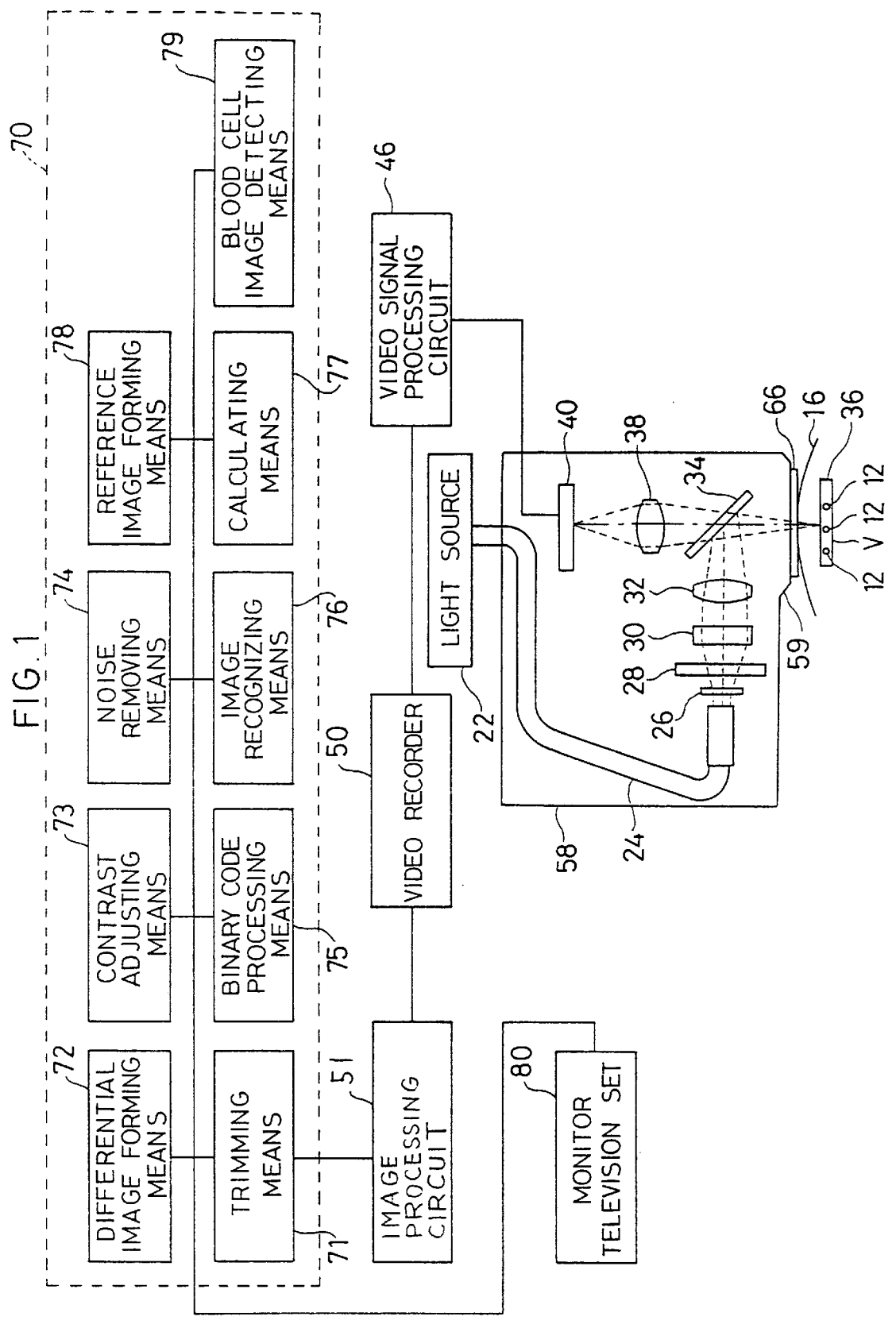

FIG. 1 shows an essential structure of an embodiment of the present invention.

Light emitted from a halogen lamp 22 is directed to a diffuser 26 via an optical fiber 24. The diffuser 26 diffuses the light with a plate 28 which is uniformly irradiated. The plate 28 substantially constitutes a surface light-emitter. Via an optical system formed of lenses 30 and 32, and a dichroic mirror 34, a real image 36 of the plate 28 is formed across blood vessels 12 located inside the skin surface 16 of a living body. Incidentally a light diffusing plate, for example, a frost-type diffusing plate manufactured by Sigma Optical Apparatus, can be used as the plate 28.

Thus a region of the real image 36 including the blood vessels 12 constitutes a detection region V.

A CCD 40 receives reflected light coming from the region V via the dichroic mirror 34 and a lens 38.

In this case, only a region in the living body which has a certain depth is irradiated with light, with the result that the region receives very little scattered light coming from other portions of the living body, for example, portions located deeper than the location of the selected blood vessel.

In addition, a probe 58 accommodates the diffuser 26, the plate 28, the lens 30, 32 and 38, the dichroic mirror and the CCD 40. An end portion 59 of the probe 58 closely contacts the surface of the skin 16 with a plastic or glass transparent plate 66 sandwiched therebetween to provide a stable image free of blurring.

A video signal processing circuit 46 processes an image signal output from each pixel of the CCD 40. Then the video signal processing circuit 46 consecutively forms one frame of image every one thirtieth of a second. Then a video recorder (for example, a laser disk recorder) 50 records the frame images formed.

Reference numeral 51 designates an image processing circuit for adjusting the contrast of the image, for example, an analog preprocessor HK-7000 (manufactured by Minolta). Further, reference numeral 70 designate an analyzing device for analyzing the number of blood cells contained in the detection region by processing a photographed image. For example, a device comprising an image processing computer (such as a Quadra 800 manufactured by Apple Computer) and a video capture board IQ-V 50 (manufactured by Hamamatsu Photonics) can be used as an analyzing device.

Then the analyzing device 70 includes trimming device 71 for trimming and outputting a predetermined region of an image frame output by the image processing circuit 51; reference image forming device 78 for forming a reference image by using one or more output images output by the trimming device 71; a differential image forming device 72 for calculating a difference in each pixel value (data) between the images output by the trimming device 71 and the reference image thereby forming a differential image based on the difference in pixel values thus calculated; a contrast adjusting device 73 for adjusting the contrast of the differential image; a noise removing device 74 for removing noise from the differential image; a binary code processing device 75 for binary coding the pixel values of the differential image by using a threshold value; a blood cell image detecting device 79 for detecting a blood cell image from an image formed by a binary coded pixel value; an image recognizing device 76 for comparing a detected blood cell image with a predetermined reference image to recognize the kind of the blood cell in the image; and a calculation device 77 for calculating the number of blood cells per unit volume from the blood cell image. Then a monitor television set 80 monitors each image formed in the analyzing device 70.

Two procedures for counting the number of white blood cells will be described hereinbelow which use the above analyzing device 70.

(1) A procedure in which one image frame serves as a reference Image

Figure 3:
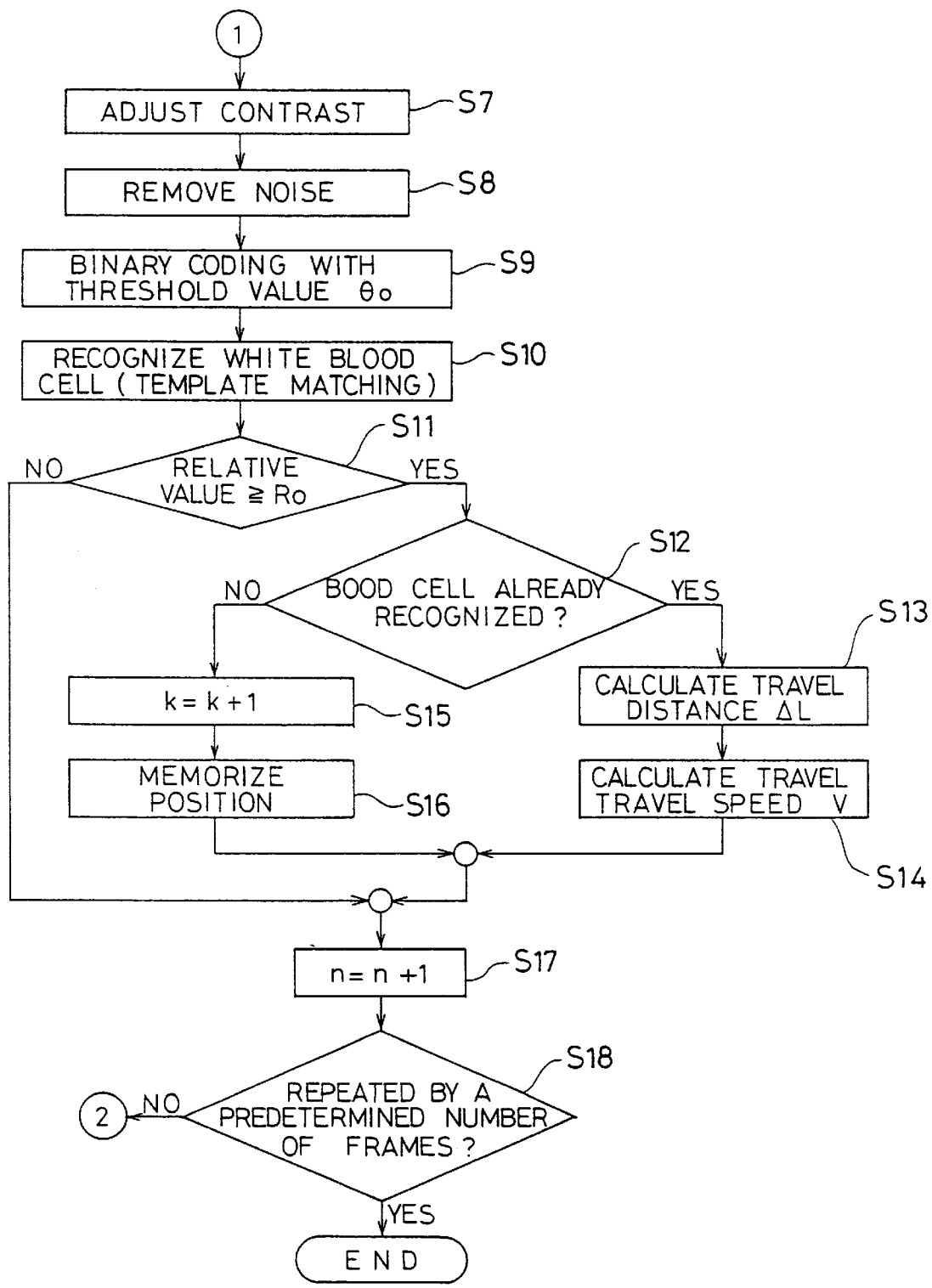

FIGS. 2 and 3 are flowcharts showing a procedure in which one image frame serves as a reference image.

Here the analyzing device read images A(0), A(1), A(2), . . . , A(n), . . . , one by one in a plural frame long or field long time sequence.

A first step is to read the image A(0) in the first frame (Step S1), followed by trimming an image B(0) in a region containing the blood vessel (Step S2). A third and a fourth step are to read the image A(1) in the subsequent frame (Steps S3, S4) followed by correcting the relative position shift of the images (Step S4a). A fifth step is to trim an image B(1) in the same region (Step S5). A sixth step is to form a differential image C(1) formed by taking a difference in each pixel value between the image B(1) and the image B(0) to form a differential image comprising the difference (Step S6). A seventh step is to adjust the contrast of the differential image (such as equalizing) (Step S7). An eighth step is to perform smoothing processing for removing the noise (Step S8).

Then the following step is to binary code, by using a threshold value, the pixel values in the image thus processed (Step S9). The following step is to detect the blood cell image and recognize white blood cells from the detected blood cell image. For this purpose, reference images (templates) are overlapped to perform template matching (step 10).

The subsequent step is to examine the value of overlap (relative value) R which exceeds a definite value $R_o$ (Step S11). When all the values R are less than $R_o$, a judgment is made that a white blood cell is not present. On the other hand, when some values R exceed $R_o$, it is recognized that white blood cells are present at a location where R assumes the maximum value. As a means for recognizing white blood cells, the size of the binary image is compared with a predetermined value.

In this manner, the above method allows recognizing white blood cells that are flowing relatively fast in the central portion of the blood vessel and white blood cells flowing relatively slowly along the wall of the blood vessel.

When the white blood cells thus recognized are the same as white blood cells that are recognized in the preceding differential image, the next step is to calculate the distance ΔL between the white blood cells and the speed thereof (Steps S12, S13 and S14).

When white blood cells are newly recognized, the step is to record the position where white blood cells are recognized with the count number given by K+1 where K represents the number of white blood cells that are counted (Step S15 and S16). Then the following step is to repeat the procedure that comes after step S4 (Steps S17 and S18). The subsequent step is to calculate the number of white blood cells WBC per unit volume from the following equation by using the value K and the average value Va of V:

$$WBC = A \cdot k / Va$$

(A is a constant)

By the way, when the number of white blood cells WBC is determined from capillaries, the number WBC is translated into the number of white blood cells corresponding to large and medium-size arteries and veins by using a predetermined function.

Then images obtained by the monitor television set 80 will be explained in conjunction with the flowchart shown in FIGS. 2 and 3.

Figure 4:
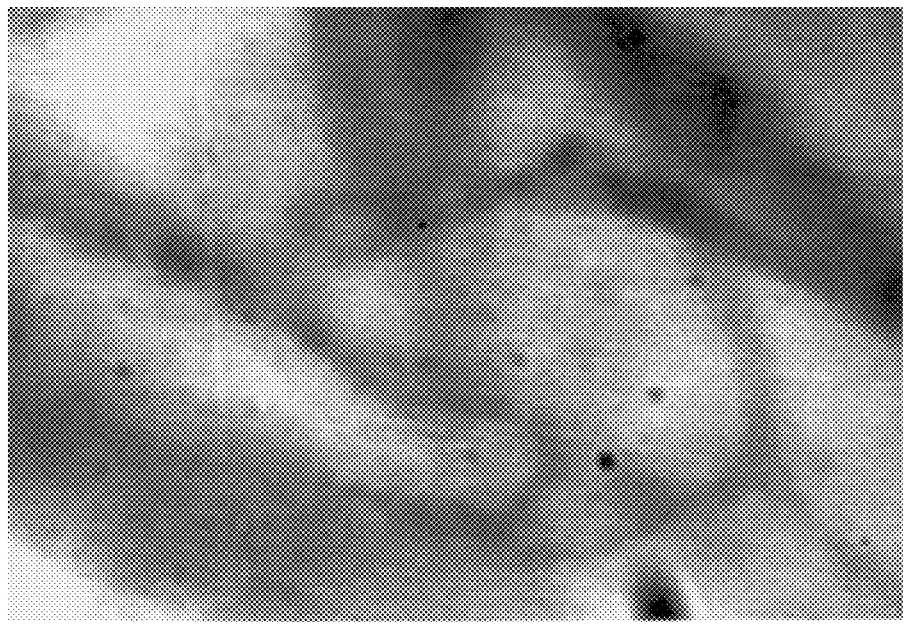
FIGS. 4–18 are examples of images obtained in an embodiment of the present invention.

FIG. 4 shows an image A(0) read at step S1. Since the image is static, capillaries can be observed, but the presence of white blood cells cannot be confirmed at all.

Figure 5:
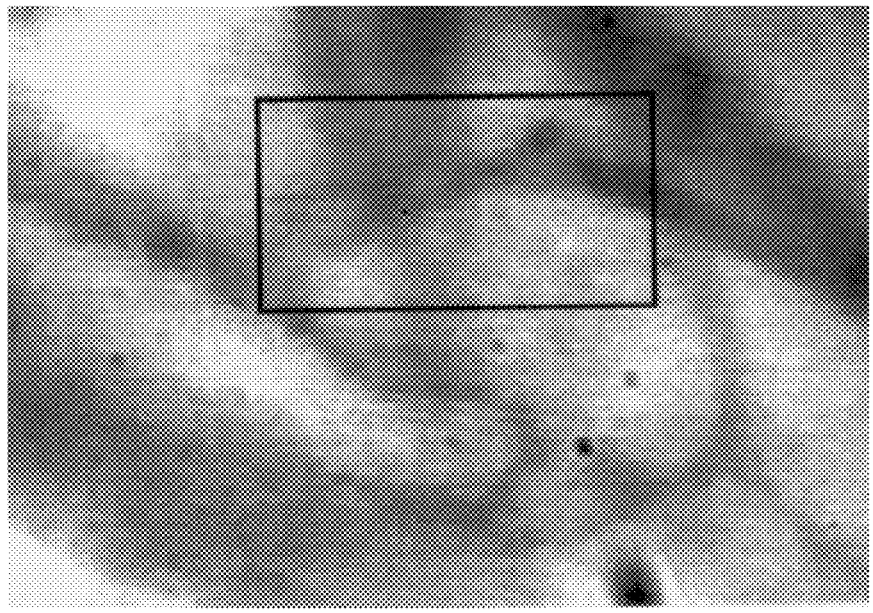

FIG. 5 is a view showing a trimmed region in the image A(0) when the image B(0) is trimmed at Step S1.

Figure 6:
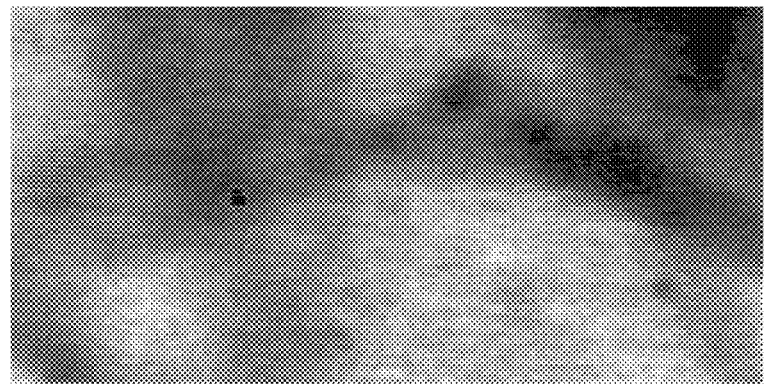
Figure 7:
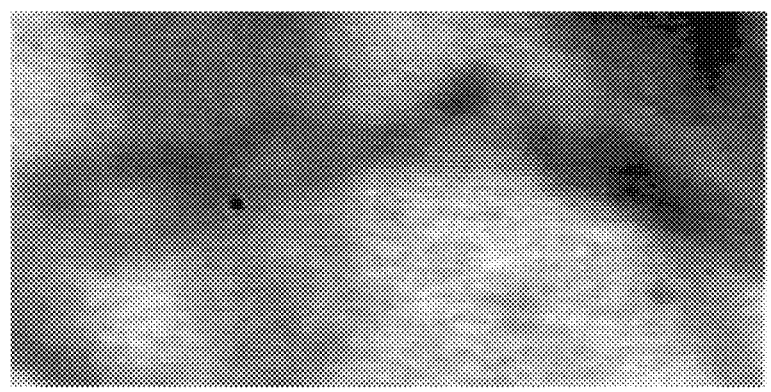
Figure 8:
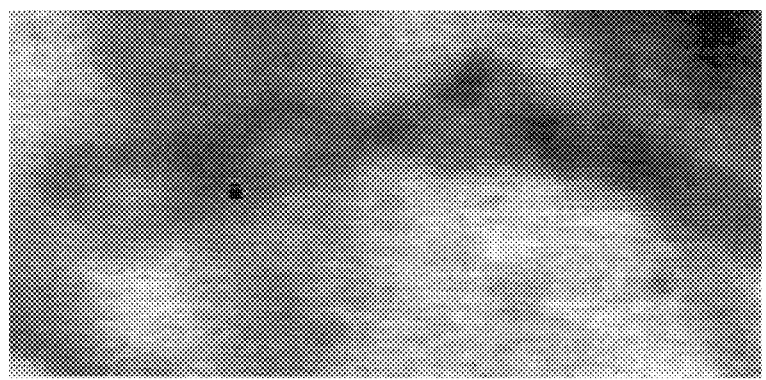

FIGS. 6 through 8 are views showing images B(0), B(1) and B(2) trimmed at Step S2, respectively.

Figure 9:
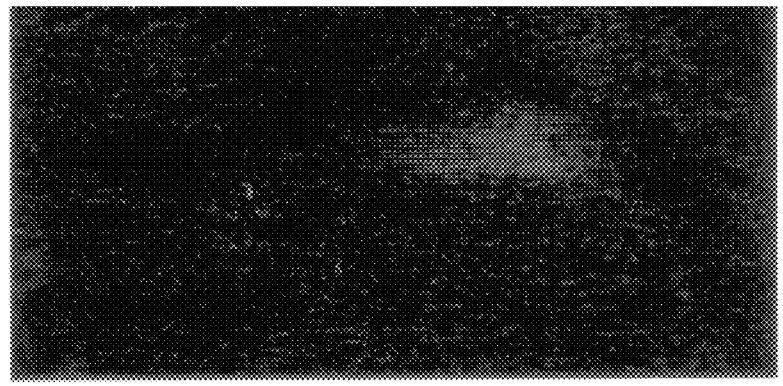
Figure 10:
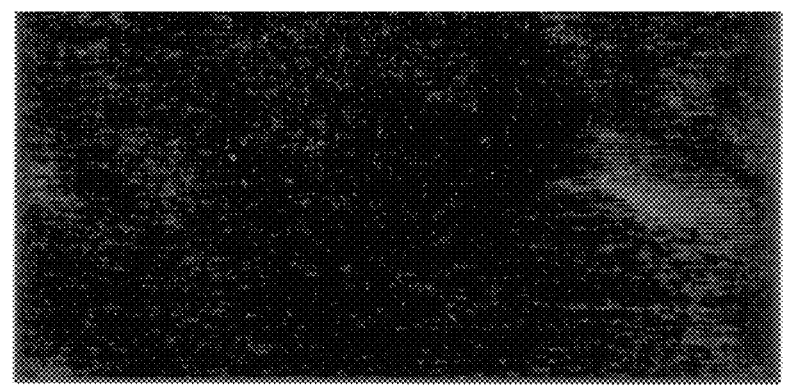

FIGS. 9 and 10 are views showing images C(1) and C(2) formed at step S6.

Figure 11:
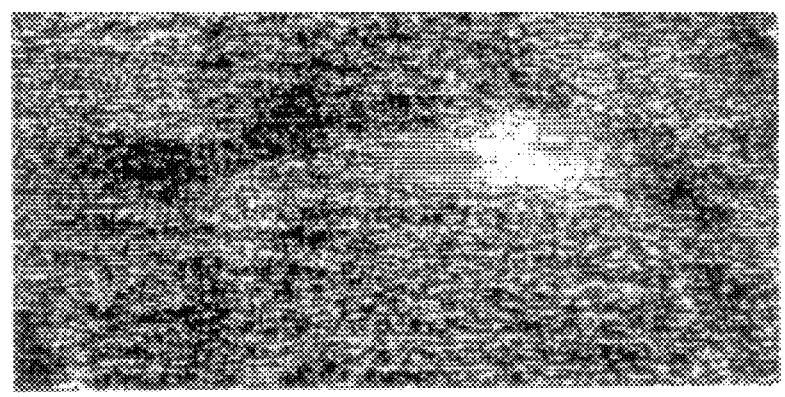
Figure 12:
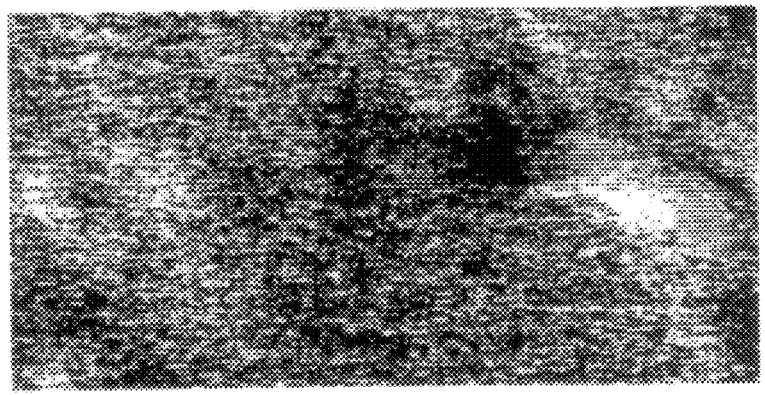
Figure 13:
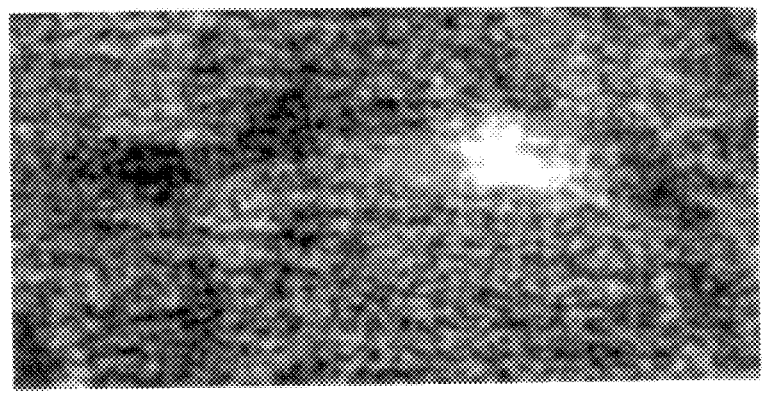
Figure 14:
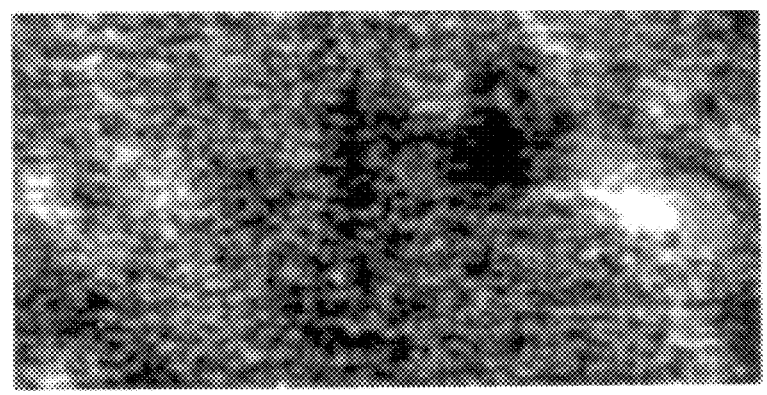

FIGS. 11 and 12 are views which emphasize the contrast of images C(1) and C(2) which were formed at Step S7. At step S7, the images of white blood cells emerge. These images are subjected to the noise removing process at step S8. Thus, the results as shown in FIGS. 13 and 14 are produced.

Figure 15:
Figure 16:
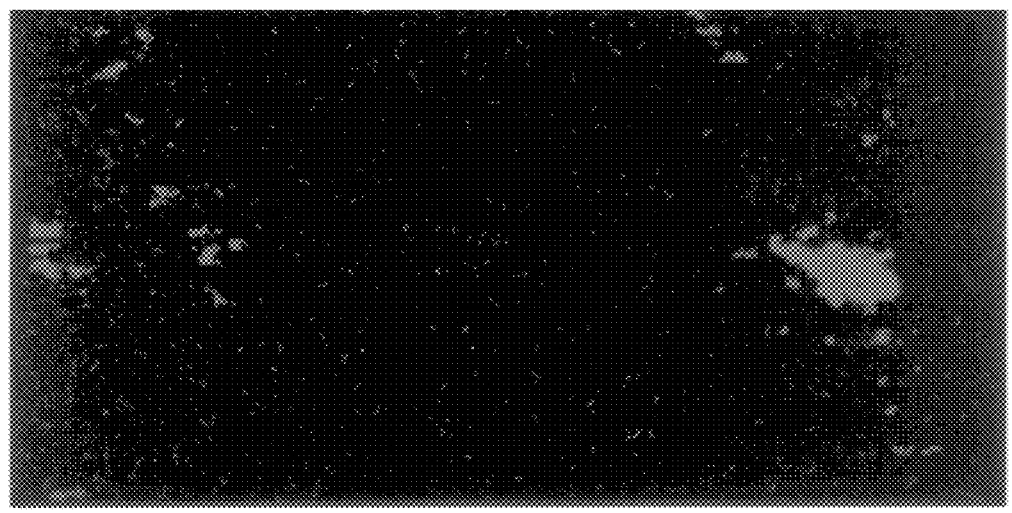
Figure 17:
Figure 18:
Figure 19:
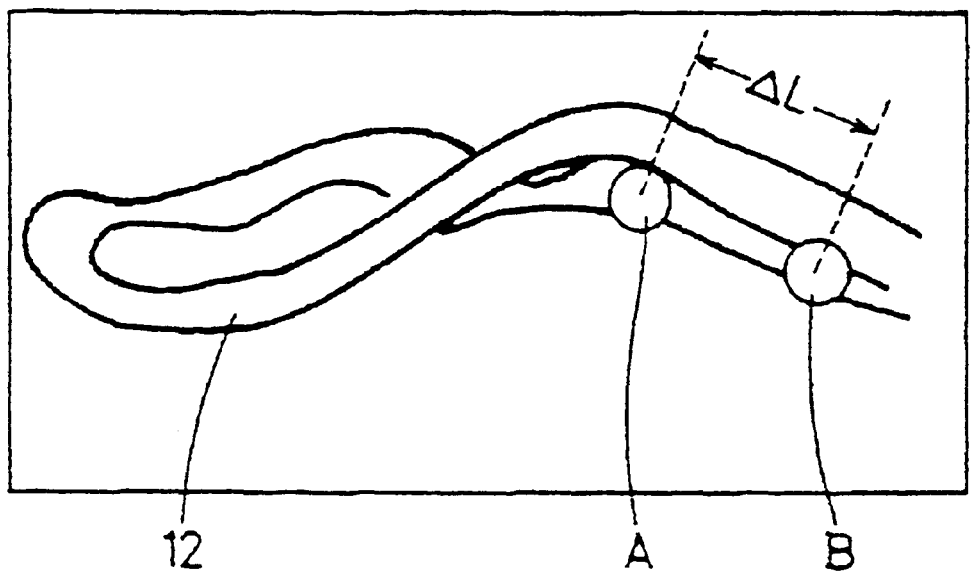
FIG. 19 is a schematic view showing the leukocyte designated in FIGS. 17 and 18.

In the subsequent process, these images are binary coded to produce images as shown in FIGS. 15 and 16. FIGS. 17 and 18 show images in a state in which circular reference images having a predetermined area are overlapped on blood cell images produced in FIGS. 15 and 16. It is observed from these images that one white blood cell moves from position A to position B during one photographing cycle of one thirtieth of a second.

Then the next step is to actually measure the distance ΔL from position A to position B thereby calculating a flow rate V of the white blood cell.

Additionally, the number k of white blood cells that appear is counted. From these values, the actual number of white blood cells WBC are counted as described above.

Figure 20:
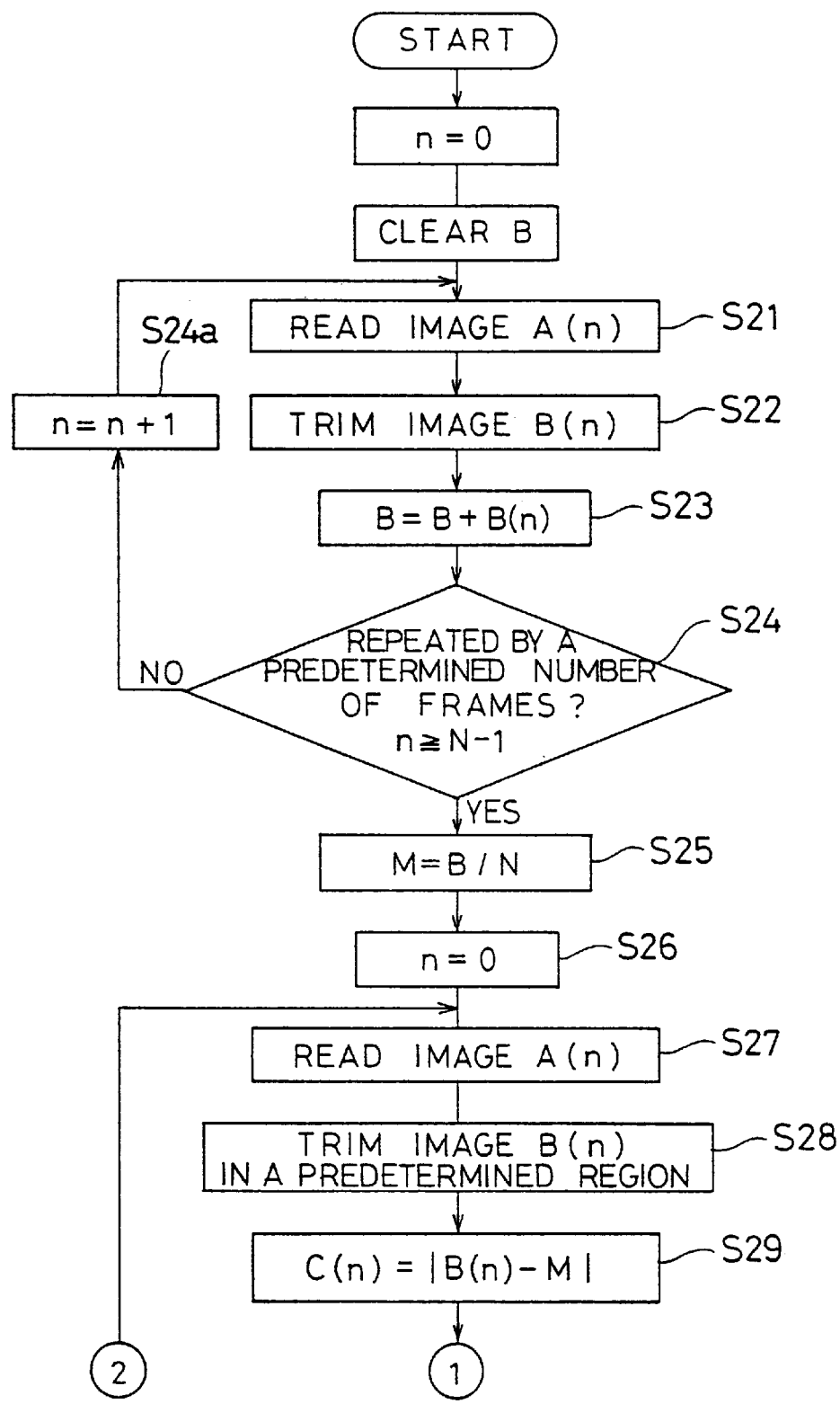
FIG. 20 is a flowchart snowing another procedure of an embodiment of the present invention.

(2) A procedure in which the average of images in plural frames serves as a reference image FIG. 20 is a flowchart showing the procedure in this case. Incidentally, Step S29 in the flow in FIG. is are connected to Step S7 in FIG. 3 and Step S18 in FIG. 3 is connected to Step S27 in FIG. 20.

In this case, the analyzing device 70 subsequently reads and processes images A(0), A(1), A(2), - - - , A(n), - - - in a plural frames or fields long time sequence which are recorded in a video recorder 50.

A first step is to read an image in a first frame to trim an image B(0) in a region containing blood vessels from the image A(0) (Steps 21 and 22). A third step is to accommodate the image B(0) in a memory region of the reference image forming device 78 (Step S23). The subsequent step is to judge whether or not the above operation is repeated by a predetermined number of frames N (Step S24). When it has been judged that the operation is not completed, reading and trimming operations are repeated as described above with respect to an image A(1) (Step S24a), followed by reading and trimming images as described above (Steps S21 and S22) to substitute the image B(0) already accommodated in the memory region of the reference image forming device 78 into the image B(0)+B(1) (Step S23).

The above operation is repeated by a predetermined number of frames N (Step S24) to calculate the total of N frame long images B=B(1)+B(2)+ - - - +B(N). Then the reference image M is determined by calculating B/N (Steps S24 and S25).

The subsequent step is to read the image A(0) in the first frame again (Steps S26 and S27) followed by trimming the image B(0) in the same region as described above (Step S28). Then a difference in pixel value between the image B(0) and the reference image M is calculated to form a differential image C(0) in which the difference constitutes the pixel value (Step S29).

The foregoing procedure shown in FIG. 3 is carried out with respect to images in a predetermined number of frames to determine the travel distance ΔL of the white blood cell and the speed V thereof and to calculate the number of white blood cells WBC per unit volume.

In this manner, the present invention allows recognizing blood cells with ease and counting the number thereof by cyclically photographing the blood flowing through the blood vessel without extracting blood to form a differential image showing a difference between two images.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A non-invasive blood analyzer comprising:
   light applying means for applying light to a detection region including a blood vessel in a living body;
   capturing means for capturing an image of the detection region to which the light is applied; and
   analyzing means for processing the captured image to analyze blood cells in the blood vessel included in the detection region,
   the analyzing means including,
      reference image forming means for calculating an average of pixel information of at least two of a plurality of images captured by the capturing means in the same detection region, and for forming a reference image from the calculated average pixel information,
      differential image forming means for calculating a difference in pixel information between the reference image and another one of the plurality of captured images and for forming a differential image from the calculated difference in pixel information, and
      blood cell image detecting means for detecting a blood cell image from the differential image.

2. A non-invasive blood analyzer according to claim 1 wherein the analyzing means further includes binary code processing means for binary coding the differential image.

3. A non-invasive blood analyzer according to claim 1 wherein the analyzing means further includes means for comparing the detected blood cell image with the reference image to recognize the blood cell.

4. A non-invasive blood analyzer according to claim 1 wherein the blood cell detecting device detects a white blood cell image.

5. The non-invasive blood analyzer of claim 1, wherein the detection region of the living body is untainted.

6. The non-invasive blood analyzer of claim 1, wherein no image-enhancing substance is applied to the living body prior to applying light to the detection region.

7. The non-invasive blood analyzer of claim 1, further comprising:
   a housing, containing at least the light applying means and capturing means, for contacting the living body through a transparent plate.

8. A non-invasive blood analyzer comprising:
   light applying means for applying light to a detection region including a blood vessel in a living body;
   capturing means for capturing an image of the detection region to which the light is applied; and
   analyzing means for processing the captured image to analyze blood cells in the blood vessel included in the detection region, analyzing means including,
   reference image forming means for forming a reference image of at least one of a plurality of images captured by the capturing means in the detection region,
   differential image forming means for calculating a difference in pixel information between the reference image and another one of the plurality of captured images and for forming a differential image from the calculated difference in pixel information,
   blood cell image detecting means for detecting a blood cell image from the differential image,
   means for calculating a number of blood cells detected and a travel distance of at least one blood cell based on a plurality of blood cell images detected by the blood cell image detecting means, means for calculating a travel speed of the at least one blood cell from the calculated travel distance and image capturing cycle, and means for calculating a number of blood cells per unit volume based on the number of blood cells detected and the calculated travel speed of the at least one blood cell.

9. A method for non-invasively analyzing blood comprising the steps of:

applying light to a detection region including a blood vessel in a living body;

capturing an image of the detection region to which the light is applied;

forming a reference image by using a calculated average of pixel information of at least two of a plurality of images captured in the same detection region;

calculating a difference in pixel information between the reference image and another one of the plurality of captured images to form a differential image from the calculated difference in pixel information; and detecting a blood cell image from the differential image to analyze the blood cell.

10. The method for analyzing blood of claim 9, further comprising the step of comparing the detected blood cell with the reference image to recognize the blood cell.

11. A non-invasive blood analyzer comprising:

light applying means for applying light to a detection region including a blood vessel in a living body;

capturing means for capturing an image of the detection region to which the light is applied; and analyzing means for processing the captured image to analyze blood cells in the blood vessel included in the detection region, the analyzing means including, reference image forming means for forming a reference image of at least one of a plurality of images captured by the capturing means in the detection region, differential image forming means for calculating a difference in pixel information between the reference image and another one of the plurality of captured images and for forming a differential image from the calculated difference as in pixel information, and blood cell image detecting means for detecting a blood cell image from the differential image, wherein the non-invasive blood analyzer further comprises a transparent plate; and a housing, containing at least the light applying means and the capturing means, for contacting the living body through the transparent plate.

* * * * *